United States Patent [19]

Bevilacqua

[11] 4,177,817
[45] Dec. 11, 1979

[54] DUAL TERMINAL TRANSCUTANEOUS ELECTRODE

[75] Inventor: Albert J. Bevilacqua, Downers Grove, Ill.

[73] Assignee: C. R. Bard, Inc., Murray Hill, N.J.

[21] Appl. No.: 874,233

[22] Filed: Feb. 1, 1978

[51] Int. Cl.² ............................................. A61N 1/04
[52] U.S. Cl. .................................... 128/802; 128/803
[58] Field of Search ............... 128/417, 2.1 E, 2.06 R, 128/404, 410, 411, 416, 418, 172.1, DIG. 4

[56] References Cited

U.S. PATENT DOCUMENTS

| | | | |
|---|---|---|---|
| 2,590,876 | 4/1952 | Landauer | 128/417 |
| 3,386,445 | 6/1968 | McDonald | 128/417 |
| 3,387,608 | 6/1968 | Figar | 128/2.06 E |
| 3,472,233 | 10/1969 | Sarbacher | 128/417 X |
| 3,805,769 | 4/1974 | Sessions | 128/2.06 E |
| 3,828,766 | 8/1974 | Krasnow | 128/2.1 E |
| 3,868,946 | 3/1975 | Hurley | 128/2.1 E |
| 3,964,469 | 6/1976 | Manley | 128/2.1 E |
| 3,977,392 | 8/1976 | Manley | 128/2.1 E |
| 3,993,049 | 11/1976 | Kater | 128/2.06 E |
| 4,082,086 | 4/1978 | Page et al. | 128/2.06 E |
| 4,082,087 | 4/1978 | Howson | 128/2.06 E |

FOREIGN PATENT DOCUMENTS

264608  6/1970  U.S.S.R. ............................ 128/2.1 E

*Primary Examiner*—Lee S. Cohen
*Attorney, Agent, or Firm*—Trexler, Wolters, Bushnell & Fosse, Ltd.

[57] ABSTRACT

There is disclosed, a disposable, preferably pregelled electrode construction for the transcutaneous application of electrical pulses to provide a stimulus thereby producing involuntary neuromuscular contractions. The electrode is comprised of a base section formed from non-conductive material such as cellular plastic foam. At least two closed-bottom reservoir chambers are formed in the base section for housing a quantity of electrolytic gel, with a cellular sponge-like pad disposed in each chamber and saturated with said electrolytic gel. An electrical terminal assembly is provided for each reservoir chamber in the form of a two-piece snap-type fastener mounted to the base section through the bottom wall of the chamber. Each terminal assembly includes an inner eyelet in surface engagement with the gel pad, and an outer stud engaged with said eyelet for connection to an electrical lead from a pulse generator. The respective reservoir chambers are spaced each from the other by a portion of the base section designated as a barrier segment. The thickness of the material providing the base section, and the minimum width of the barrier segment are selected to insure that upon application of the electrode to the skin of a patient, that the respective chambers, gel pads and terminal assemblies are electrically insulated each from the other by the base section material. Accordingly, upon the application of a pulse to the electrode, current will pass through the underlying tissue in traveling from terminal to terminal.

4 Claims, 4 Drawing Figures

U.S. Patent  Dec. 11, 1979  4,177,817
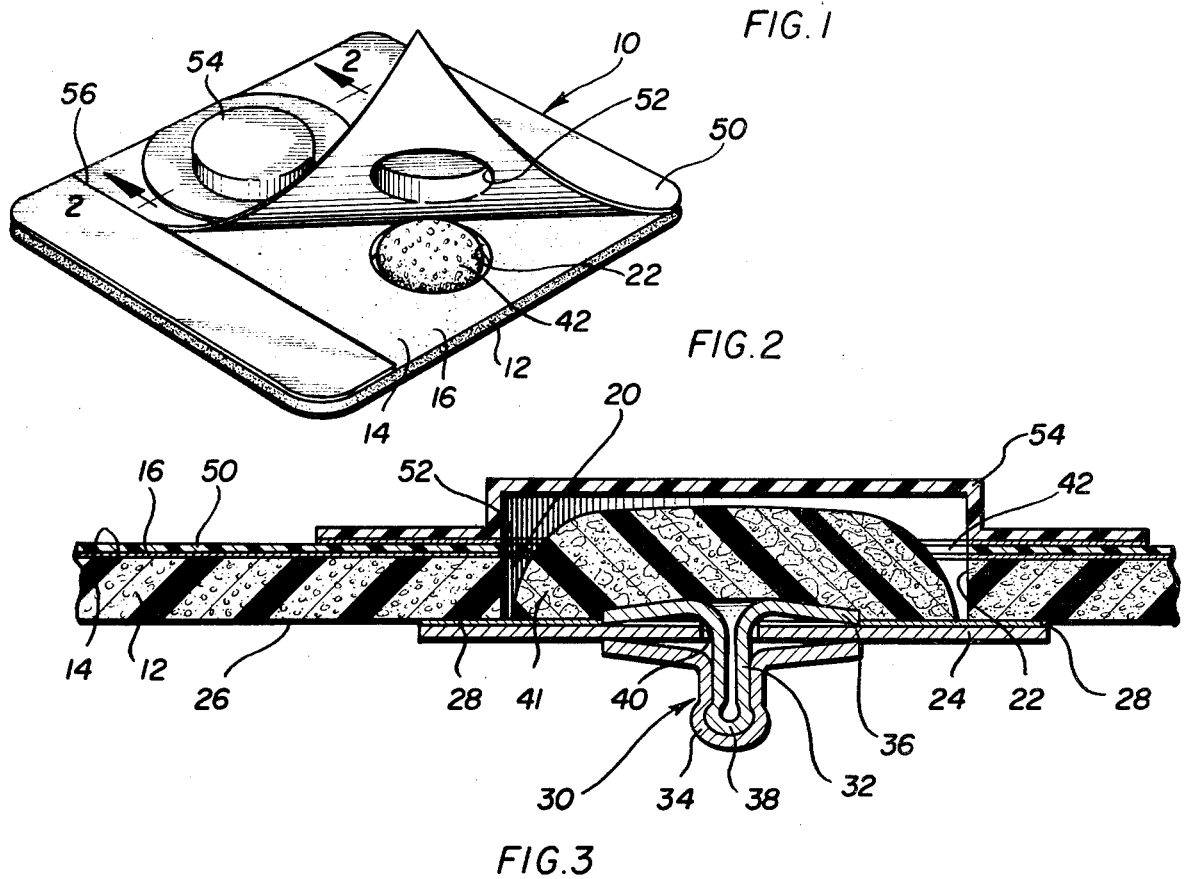
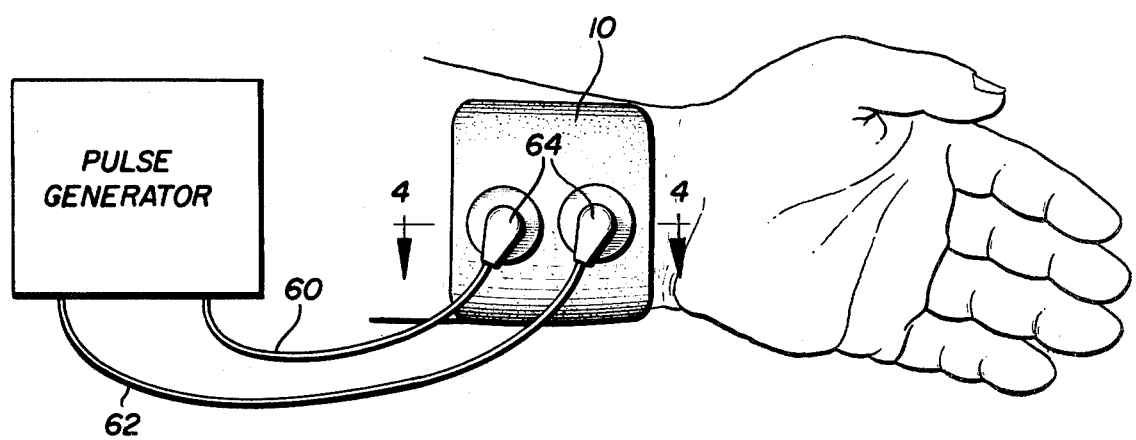

DUAL TERMINAL TRANSCUTANEOUS ELECTRODE

BACKGROUND OF THE INVENTION

The present invention relates to an electrode design for the application of neurological stimulus to a patient in the form of current pulses from a pulse generator, and most particularly to a novel dual-terminal electrode designed particularly for the controlled stimulation of underlying nerve tissue to produce involuntary muscle contractions or responses that can be employed as a monitoring tool by anesthesiologists.

In recent years, anesthesiologists have become concerned with the monitoring and control of the effects of nondepolarizing neuromusclar blocking agents on patients both during and after surgical procedures. As is well known, anesthetization procedures are performed using a number of anesthetizing agents, the type and flow rate of the respective agents being controlled by the anesthesiologist during the surgical procedures. In this regard, the anesthesiologist will utilize some form of muscle relaxant and these are often nondepolarizing, requiring the administration of a reversing agent after the surgical procedure to reverse the muscle blocking effects thereof.

One method which has been employed to monitor the effects of these nondepolarizing agents, is to electrically stimulate the patient's nerve tissue to produce involuntary muscle contraction. Since the strength and frequency of the pulse applied is known and can be controlled, a comparison between the patient's reactions prior to administration of the anesthetic and at intervals during and after anesthetization provide an indication as to the muscle blocking effect of the relaxant. Accordingly, the anesthesiologist monitoring of the involuntary muscle contraction provides an aid to the anesthesiologist in determining the dosage of the relaxant to be applied to the patient. Further, with regard to non-polarizing reactions, the degree of involuntary contraction observed after the surgical procedure, also provides a useful aid in determining the dosage of the reversing agent to be administered to the patient. A more detailed discussion of this general procedure can be found in U.S. Pat. Nos. 3,364,929 and 3,565,080.

The electrode design of the present invention provides a convenient and reliable construction that enables the proper application of nerve stimulating pulses, thereby aiding in the overall monitoring process. In this regard, the electrical terminals required in the transcutaneous application of current to the nerve tissue are provided in a single electrode structure, and are isolated electrically, so as to insure that the current passes through the patient's body tissue. The electrode is also disposable and preferably pre-gelled with the desired quantity of electrolytic gel being provided in the reservoir chambers. More specifically, the diameter and depth of the reservoir chamber, and the spacing between the respective chambers provided by the barrier segment of the base section are parameters which are determined in relation to the quantity of gel to be employed, and are selected such that upon mounting of the electrode to the skin of a patient, the electrical isolation of the respective chambers will be maintained and the gel from the respective chambers will not be co-mingled. Accordingly, upon the application of voltage across the respective terminals, a current pulse will flow from the terminal means and associated gel of a first one of said reservoir chambers to and through the body tissue of the patient to the gel and terminal means of the other of said reservoir chambers. It can be appreciated, that if the respective chambers were not electrically isolated, or if the gel quantities co-mingled, current could pass along the outer skin surface and the desired transcutaneous application of pulses to the nerve tissue would not occur, or would be adversely affected.

From the above discussion, and the detailed discussion of the illustrated embodiment to follow, it is believed that the advantages and features of the invention will become apparent. In this regard, the detailed description to follow will be had in conjunction with the accompanying drawings, wherein like reference numerals are used throughout to designate similar elements and components.

BRIEF DESCRIPTION OF THE DRAWINGS

FIG. 1 is a perspective view of an electrode constructed in accordance with the present invention, with the cover for the adhesively coated surface partially removed.

FIG. 2 is a partial, sectional view taken along the line 2—2 of FIG. 1, and in the direction indicated.

FIG. 3 is a schematic representation illustrating the application of the electrode to a patient in relation to the ulnar nerve in the area of the patient's wrist.

FIG. 4 is a partial, sectional view taken along the line 4—4 of FIG. 3.

DETAILED DESCRIPTION OF THE ILLUSTRATED EMBODIMENT

The design or construction of the electrode of the present invention, which is designated generally by reference character 10, will be considered initially with regard to FIGS. 1 and 2. A discussion of the typical application or use of the electrode 10 will then be had in conjunction with FIGS. 3 and 4. In this regard, it is believed that the discussion of the application or use of the electrode 10 will highlight the contribution and importance of the various unique structural features of the electrode of the present invention, which contribute to its overall superior operational characteristics.

Accordingly, attention is initially directed to FIGS. 1 and 2 for a discussion of the general construction of the electrode 10.

More specifically, and with reference to FIGS. 1 and 2, the electrode 10 includes a base section 12 formed from a non-conductive foam-like cellular plastic material such as polyethylene or polyurethane. The upper surface 14 of the base section 12 is covered with an adhesive substance 16. A cover structure overlies and protects the adhesive coated surface 14, which cover structure will be discussed in greater detail hereinafter.

The electrode 10 includes at least two reservoir chambers and terminal assemblies. Since the respective chambers and terminal assemblies are virtually identical, discussion will be had with regard to FIG. 2 wherein one of such assemblies is illustrated. It is to be understood that the other assembly is of essentially similar construction.

Accordingly, with reference to FIG. 2, it can be seen that the base section 12 is provided with a closed bottom reservoir chamber 20. The chamber 20 in the preferred embodiment is formed by the provision of a through aperture 22 in the base section 12, and the attachment of a section or sheet of non-porous material 24 to the surface 26 of the base section, in overlying relation to the aperture 22. The sheet 24 includes an adhesive coating 28 which secures the sheet 24 to the surface 26 and also serves an additional function to be discussed hereinafter. Thus, it can be seen that the sheet 24 in effect serves as the bottom wall for the reservoir chamber 20.

A terminal assembly, designated generally 30, is carried by the sheet 24. In the illustrated embodiment, the terminal assembly 30 is in the form of a typical snap-type fastener which includes an inner element or stud 32 and an outer element or eyelet 34 engaged therewith. The inner stud 32 includes a flange portion 36 and a post portion 38 which extends through an aperture 40 formed in the sheet or base wall 24 for the chamber 20. The respective elements 32 and 34 of the terminal assembly 30 are formed of metal, or some other conductive material, with the outer element 34 being adapted for connection to lead wires of a current or pulse generator, as will be discussed more completely with regard to FIGS. 3 and 4.

With continued reference to FIG. 2, it should be noted that the diameter or cross-sectional width of the flange 36 is substantially less than the diameter of the reservoir chamber 20. Accordingly, an annular segment or portion of the adhesive coating 28 on the sheet 24 is exposed. An open cell foam-like pad 42 is engaged with the exposed portion of the adhesive surface 28, thereby to secure the pad 42 within the reservoir 20, said pad overlying the flange portion 36 of terminal 30. Further, a quantity of conductive gel, designated generally 41, is disposed within the reservoir 20. Various conductive gels are readily available and are well known to those in the art.

In addition to the above-discussed structure, the entire surface 14 of the electrode is protected by a cover structure. In this regard, the cover structure includes a sheet of non-porous material 50 which overlies the surface 14 of the electrode, and is provided with apertures 52 corresponding approximately to the apertures 22 in the base 12 which serve to form the reservoir chambers 20. The under-surface of the sheet 50 is provided with a coating which while enabling the sheet to adhere to the adhesive 16, permits removal of the sheet when desired. In this regard, coatings of this type generally employ silicon and are well known in the art. Attached to the sheet 50 in overlying relation to the aperture 52, is a cup-like structure 54. The cup-like structure 54 provides a space for reception of the gel pad 42 which extends above the adhesive surface 14. As such, the cup-like structure 54 prevents undesired compression of the gel pad 42 which would result in the gel 41 being squeezed therefrom. As an additional matter, the sheet 50 may also be provided with a score line 56 which extends across the width thereof, and which facilitates removal of a major portion of the cover, that including the caps 54, thereby exposing the adhesive surface 14 of the base section for attachment of the electrode to the skin of the user.

As will become more apparent from the discussion of the use of the electrode 10 to be had with regard to FIGS. 3 and 4, certain dimensional features of the electrode are important and must be controlled in order to obtain the desired result. In this regard, it is not intended to imply, nor is it practical to state that exact limits or dimensions must be utilized, as the critical nature of these dimensions will vary depending upon the use to which the electrodes are put and the quantity of gel employed. What is necessary, as will be discussed more fully hereinafter, is that the reservoir 20 be of sufficient volume or dimension to accept a desired quantity of gel, such that upon application of the electrode to the patient's skin, the gel will not be squeezed into the interface of the base surface 14 and the patient's skin. Also, the respective chambers 22 must be spaced or separated by a barrier or segment of non-conductive foam material so as to electrically isolate one from the other.

With reference to FIGS. 3 and 4, there is illustrated a typical use of the electrode 10 in conjunction with a pulse generator for stimulation of the ulnar nerve of a patient. In this regard, the cover structure is removed from the electrode, as indicated generally in FIG. 1, to expose the adhesive surface 14. The electrode is then applied to the patient's wrist, or some other portion of the patient's body in overlying relation to the desired nerve to be stimulated. Next, a pair of leads 60 and 62 from a pulse generator are connected to the respective terminals 30 of the electrode 10. Each lead 60 or 62 includes a snap-type connector 64 on the end thereof, which enables electrode contact to be established with the outer terminal element 34 of the snap-type fastener, which it will be recalled is in crimped engagement with the inner terminal element 38.

With reference to FIG. 4, the relationship between the respective reservoir chambers upon attachment of the electrode to the patient is shown. For purposes of description, these chambers will be designated 20A and 20B with regard to FIG. 4. Also in this FIG., there is illustrated schematically the ulnar nerve, which is designated generally 70.

Attachment of the electrode 10 to the patient is accomplished by firmly pressing the base section against the skin surface, causing the adhesively coated surface 14 to adhere to the skin. The volume of the respective reservoir chambers 20A and 20B are selected in relation to the quantity of electrode gel 41 disposed therein, so as to permit attainment of the surface-to-surface engagement without the squeezing of the electroding gel along the interface of the surface 14 and the patient's skin. Accordingly, upon proper attachment, the saturated gel pad 42, which it will be recalled extends slightly above the surface 14, will be slightly compressed, and will be in surface contact engagement with the patient's skin. The respective saturated gel pads and terminals associated with the reservoir chambers 20A and 20B will, however, be isolated electrically each from the other, by reason of the non-conductive nature of the base section 12, and most particularly due to the barrier segment 72 of said base section which separates the respective chambers 20A and 20B.

Accordingly, since the chamber 20A is insulated from the chamber 20B by section 72 upon the application of a pulsating current across the respective terminals 30, current can pass only through the patient's underlying tissue, as represented by the dotted path 78. The current will then pass out of the patient's tissue via the gel pad 42 and terminal 30 associated with the chamber 20B. The placement of the electrode is such that the current path 78 will intersect the ulnar nerve 70 thereby stimulating said nerve to produce the desired involuntary muscle contraction discussed above.

By way of example, it has been found that foam material for the base 12 on the order of 1/16th of an inch employed in conjunction with the reservoir chambers which are approximately ⅜ of an inch in diameter and which are spaced approximately ½ inch apart provide excellent results. Of course, it must be appreciated that the quantity of electrolytic gel disposed within the respective chambers must be controlled so as not to produce an overfilled condition such as would cause the gel to migrate along the interface of the electrode with the patient's skin, and thus destroy the desired, and necessary, electrical insulation between the respective chambers 20A and 20B.

Accordingly, while there is disclosed a preferred embodiment of the present invention, applicant is aware that various changes and modifications may occur to those skilled in the art upon being possessed of the knowledge contained in the subsequent disclosure and, such changes are to be understood as forming part of the present invention, insofar as they fall within the spirit and scope thereof defined in the claims appended hereto.

The invention is claimed as follows:

1. A dual terminal electrode construction for the transcutaneous application of current to a patient, such as might be employed in the electrical stimulation of nerves, said electrode comprising a pair of spaced terminal arrangements and a base member upon which said terminal arrangements are provided, said base member comprising a section of nonconductive foam material having an adhesively coated surface for affixing the electrode in engagement with the skin of a patient above the nerve to be stimulated, and a pair of spaced through apertures, a terminal arrangement associated with each said aperture and engaged with the surface of said base member opposite said adhesively coated surface, each said terminal arrangement including, a section of non-porous, adhesively coated material of substantially less area than the base member, and affixed to the base member surface opposite said adhesively coated surface in overlying relation to the associated aperture, said sections of non-porous material serving to define with said apertures, two closed bottom reservoir chambers which open to said adhesively coated surface, with said sections of non-porous material providing the bottom walls for each said reservoir chambers, a terminal member carried by each said section of non-porous material and including a surface portion in said chamber that is sized with respect to said chamber to provide an exposed portion of the adhesively coated surface of said section of non-porous material, an open cell pad disposed in each said chamber in overlying contact with the terminal member, and affixed to the exposed portion of said adhesively coated surface of the section of non-porous material defining the bottom wall of said chamber, said base member being of a thickness to provide reservoir chambers of sufficient depth to accommodate a desired quantity of electrolytic gel which impregnates said pads, and said reservoir chambers being spaced apart a distance sufficient to provide a barrier segment separating one chamber from the other chamber, said barrier segment being of sufficient width at its narrowest point such that upon the mounting of said electrode to the skin of a patient, the respective chambers and the electrolytic gel associated with said chambers are isolated electrically each from the other by said barrier segment, such that upon the application of current across said terminal elements, said current will pass through the skin of the patient.

2. An electrode construction according to claim 1 including cover structure overlying the adhesively coated surface of the base member and said reservoir chambers.

3. An electrode construction according to claim 1, wherein said terminal members comprise snap-type fasteners including an inner element and an outer element engaged through said bottoms of the chambers with the inner element of each said fastener providing the surface portion in said chamber and the outer element of said fastener providing means for connecting said electrode to a current generator.

4. A dual terminal electrode construction according to claim 1 wherein said section of non-conductive foam material providing said base member is at least one-sixteenth of an inch thick, and said barrier segment is one-half inch in width.

* * * * *